US010973490B2

United States Patent
Kawana

(10) Patent No.: US 10,973,490 B2
(45) Date of Patent: Apr. 13, 2021

(54) RADIATION IMAGE PHOTOGRAPHING APPARATUS AND RADIATION IMAGE PHOTOGRAPHING SYSTEM FOR RADIATION IMAGE PHOTOGRAPHING PROCESS AND DARK IMAGE ACQUIRING PROCESS

(71) Applicant: Konica Minolta, Inc., Tokyo (JP)

(72) Inventor: Yuki Kawana, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 16/250,613

(22) Filed: Jan. 17, 2019

(65) Prior Publication Data

US 2019/0257961 A1 Aug. 22, 2019

(30) Foreign Application Priority Data

Feb. 19, 2018 (JP) .............................. JP2018-026727

(51) Int. Cl.
*A61B 6/00* (2006.01)
*G01T 1/24* (2006.01)
(Continued)

(52) U.S. Cl.
CPC ............ *A61B 6/545* (2013.01); *A61B 6/4007* (2013.01); *A61B 6/4233* (2013.01);
(Continued)

(58) Field of Classification Search
CPC .......... A61B 6/40; A61B 6/4007; A61B 6/42; A61B 6/4208; A61B 6/4233;
(Continued)

(56) References Cited

U.S. PATENT DOCUMENTS 7,109,491 B2 * 9/2006 Shinden ................... A61B 6/00
250/370.09
7,365,337 B2 * 4/2008 Tsuchino ................. A61B 6/56
250/370.09
(Continued)

FOREIGN PATENT DOCUMENTS

JP 2012-084958 A 4/2012

OTHER PUBLICATIONS

English translation of JP2012-084958 A by Patent Translate dated Mar. 26, 2020.*

*Primary Examiner* — Allen C. Ho
(74) *Attorney, Agent, or Firm* — Lucas & Mercanti, LLP

(57) ABSTRACT

A radiation image photographing apparatus includes a hardware processor that, at a time of a radiation image photographing process, repeats a reset process of releasing a charge from a radiation detecting element by sequentially applying an on-voltage from a scan driver to scan lines, until a radiation irradiation is started, provides a predetermined waiting time to cause all switches to wait in an off-state after the reset process and before the next reset process, transitions to a charge accumulation mode of accumulating the charge in the radiation detecting element by applying an off-voltage to all scan lines, in response to radiation irradiation start, and transitions to a reading mode of releasing the charge from the radiation detecting element by applying the on-voltage to the scan lines, and performing an image data reading process by converting the released charge into image data, when a predetermined accumulation time has elapsed.

6 Claims, 12 Drawing Sheets

(51) Int. Cl.
*H04N 5/361* (2011.01)
*H04N 5/32* (2006.01)

(52) U.S. Cl.
CPC .......... *A61B 6/4283* (2013.01); *A61B 6/4405* (2013.01); *A61B 6/4411* (2013.01); *A61B 6/4452* (2013.01); *A61B 6/542* (2013.01); *A61B 6/563* (2013.01); *A61B 6/566* (2013.01); *G01T 1/247* (2013.01); *H04N 5/32* (2013.01); *H04N 5/361* (2013.01)

(58) Field of Classification Search
CPC ....... A61B 6/4283; A61B 6/44; A61B 6/4405; A61B 6/4411; A61B 6/4452; A61B 6/54; A61B 6/542; A61B 6/545; A61B 6/56; A61B 6/563; A61B 6/566; G01T 1/247
USPC ................ 378/62, 91, 98.8, 189; 250/370.09
See application file for complete search history.

(56) References Cited

U.S. PATENT DOCUMENTS

| | | | | |
|---|---|---|---|---|
| 7,751,529 B2* | 7/2010 | Ohara | ...................... | A61B 6/00 378/116 |
| 8,193,509 B2* | 6/2012 | Niekawa | .............. | A61B 6/4233 250/370.09 |
| 8,399,846 B2* | 3/2013 | Niekawa | .............. | A61B 6/4233 250/370.08 |
| 8,625,742 B2* | 1/2014 | Iwashita | .............. | A61B 6/4266 378/116 |
| 8,642,970 B2* | 2/2014 | Iwakiri | ................... | G01T 1/247 250/370.08 |
| 8,664,615 B2* | 3/2014 | Amitani | .............. | A61B 6/4283 250/370.09 |
| 8,705,700 B2* | 4/2014 | Eguchi | ................ | A61B 6/4233 378/116 |
| 8,785,871 B2* | 7/2014 | Muraoka | ............. | A61B 6/4233 250/370.09 |
| 8,785,876 B2* | 7/2014 | Tajima | ................. | A61B 6/4233 250/363.02 |
| 8,847,138 B2* | 9/2014 | Sugawara | ............ | H04N 5/3205 250/208.1 |
| 8,866,095 B2* | 10/2014 | Oguma | ................ | A61B 6/4233 250/370.09 |
| 8,885,909 B2* | 11/2014 | Takagi | ..................... | G06T 5/20 382/132 |
| 8,942,350 B2* | 1/2015 | Iwase | ..................... | G01T 1/243 378/901 |
| 8,983,035 B2* | 3/2015 | Noma | ................... | A61B 6/548 378/97 |
| 9,035,263 B2* | 5/2015 | Iwata | .................... | G01T 1/2018 250/366 |
| 9,050,059 B2* | 6/2015 | Kuwabara | .............. | A61B 6/542 |
| 9,063,236 B2* | 6/2015 | Shikino | .................... | G01T 1/17 |
| 9,078,624 B2* | 7/2015 | Sugizaki | ............... | G01T 1/2928 |
| 9,128,368 B2* | 9/2015 | Tajima | ................... | G03B 42/02 |
| 9,155,177 B2* | 10/2015 | Kikuchi | .................. | H05G 1/08 |
| 9,186,118 B2* | 11/2015 | Yonekawa | .......... | A61B 6/4233 |
| 9,247,163 B2* | 1/2016 | Sato | .......................... | G01T 1/17 |
| 9,259,201 B2* | 2/2016 | Sato | ........................ | A61B 6/542 |
| 9,288,409 B2* | 3/2016 | Iwashita | ................ | H04N 5/361 |
| 9,301,725 B2* | 4/2016 | Kaneko | ................ | A61B 6/4233 |
| 9,341,723 B2* | 5/2016 | Niekawa | ............... | H04N 5/32 |
| 9,405,183 B2* | 8/2016 | Ando | ..................... | A61B 6/4266 |
| 9,453,923 B2* | 9/2016 | Eguchi | ................. | A61B 6/4233 |
| 9,521,986 B2* | 12/2016 | Ozawa | .................. | A61B 6/548 |
| 9,661,728 B2* | 5/2017 | Eguchi | .................... | H05G 1/08 |
| 9,668,331 B2* | 5/2017 | Takahashi | ............... | H04N 5/32 |
| 9,750,477 B2* | 9/2017 | Kitagawa | ............. | G01T 1/2018 |
| 9,753,158 B2* | 9/2017 | Nishino | .................. | G01T 1/247 |
| 9,774,794 B2* | 9/2017 | Sakino | .................... | H04N 5/32 |
| 9,780,128 B2* | 10/2017 | Tajima | .................. | A61B 6/585 |
| 9,784,856 B2* | 10/2017 | Kubota | .................... | A61B 6/56 |
| 9,793,305 B2* | 10/2017 | Tajima | .................. | H05G 1/44 |
| 9,826,946 B2* | 11/2017 | Ota | ..................... | A61B 6/4233 |
| 9,848,845 B2* | 12/2017 | Tajima | .................... | H04N 5/32 |
| 9,855,018 B2* | 1/2018 | Hamano | ................ | A61B 6/563 |
| 9,880,111 B2* | 1/2018 | Oda | ........................ | A61B 6/467 |
| 9,892,521 B2* | 2/2018 | Enomoto | .............. | A61B 6/589 |
| 9,931,092 B2* | 4/2018 | Tajima | .................... | A61B 6/488 |
| 9,973,988 B2* | 5/2018 | Ando | .................. | H04W 36/20 |
| 10,022,102 B2* | 7/2018 | Okada | .................... | H05G 1/56 |
| 10,074,679 B2* | 9/2018 | Tajima | ............. | H01L 27/14605 |
| 10,149,656 B2* | 12/2018 | Takagi | .................. | A61B 6/505 |
| 10,206,647 B2* | 2/2019 | Hiroshige | ............ | A61B 6/4233 |
| 10,251,616 B2* | 4/2019 | Maruta | .................. | A61B 6/482 |
| 10,327,729 B2* | 6/2019 | Hayashi | ................ | A61B 6/566 |
| 10,335,110 B2* | 7/2019 | Kawana | .................. | A61B 6/54 |
| 10,342,508 B2* | 7/2019 | Matsushita | .......... | A61B 6/4266 |
| 10,349,914 B2* | 7/2019 | Takenaka | ............. | G01T 1/2018 |
| 10,413,269 B2* | 9/2019 | Nagano | ................... | A61B 6/06 |
| 10,416,323 B2* | 9/2019 | Ryu | ......................... | A61B 6/54 |
| 10,440,290 B2* | 10/2019 | Kikuchi | ................... | H04N 5/32 |
| 10,451,503 B2* | 10/2019 | Kikuchi | ................. | G01P 15/0891 |
| 10,470,727 B2* | 11/2019 | Ota | .......................... | G01T 7/00 |
| 10,481,282 B2* | 11/2019 | Eguchi | .................... | G01T 1/247 |
| 10,488,534 B2* | 11/2019 | Kawaguchi | .......... | A61B 6/4283 |
| 10,520,804 B2* | 12/2019 | Miyoshi | ................ | A61B 6/102 |
| 10,524,746 B2* | 1/2020 | Maruta | ................. | A61B 6/4283 |
| 10,539,692 B2* | 1/2020 | Kosuge | .................. | H04N 5/32 |
| 10,561,389 B2* | 2/2020 | Hiroshige | .............. | A61B 6/54 |
| 10,568,595 B2* | 2/2020 | Hosoki | .................... | A61B 6/54 |
| 10,605,747 B2* | 3/2020 | Ubukata | ................... | G01T 1/17 |
| 10,628,923 B2* | 4/2020 | Takagi | ................. | A61B 6/5252 |
| 10,716,522 B2* | 7/2020 | Sato | ........................ | H04N 5/353 |
| 10,729,393 B2* | 8/2020 | Fujiyoshi | .............. | H04N 5/32 |
| 10,762,384 B2* | 9/2020 | Ito | ........................ | A61B 6/5235 |
| 10,788,592 B2* | 9/2020 | Koeda | ................... | G01T 1/2018 |

* cited by examiner

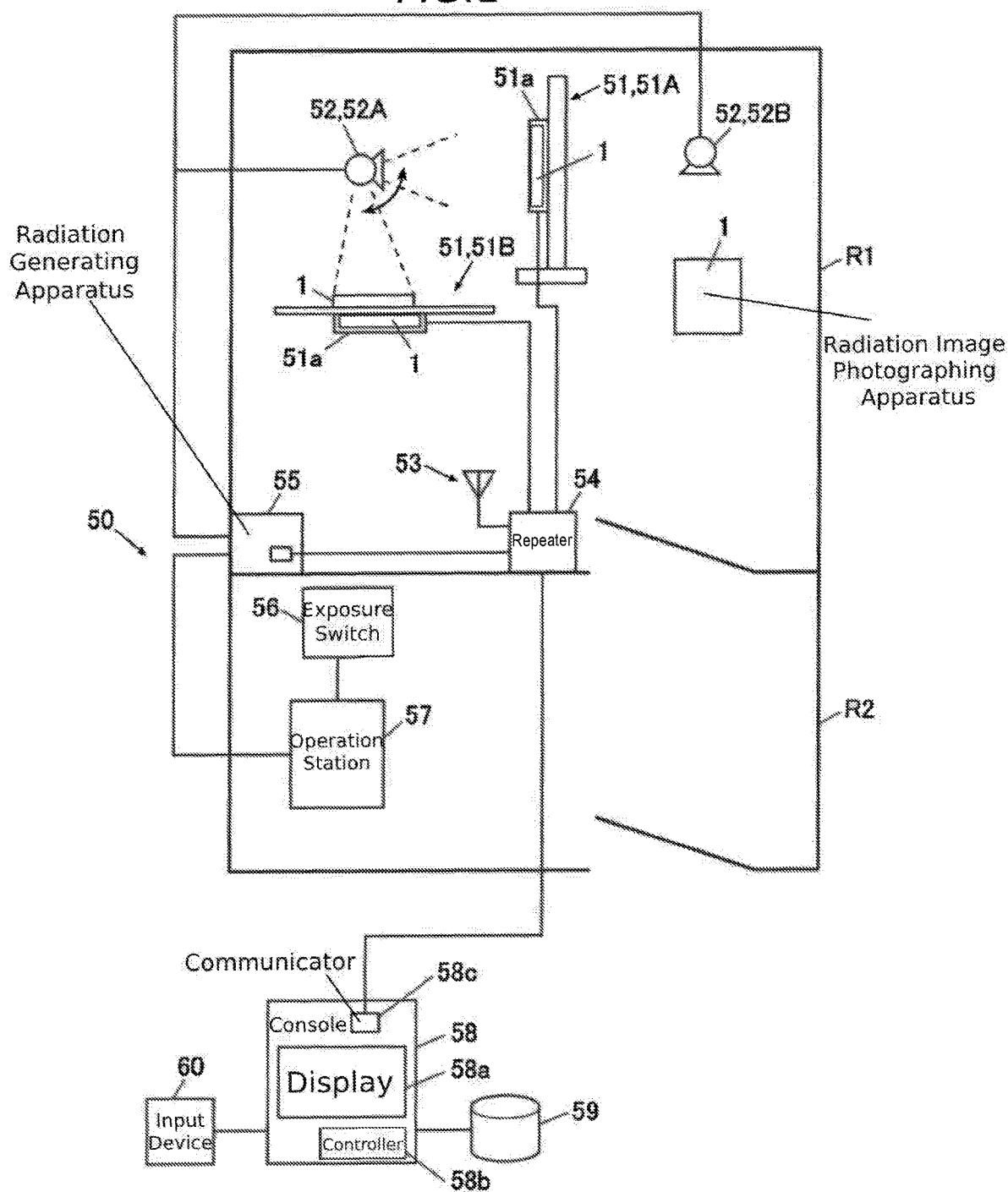

FIG.2A  FIG.2B  FIG.2C
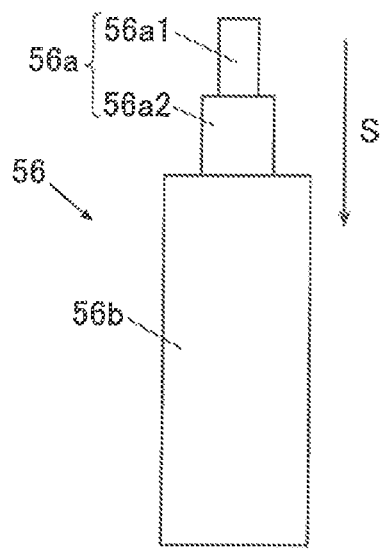
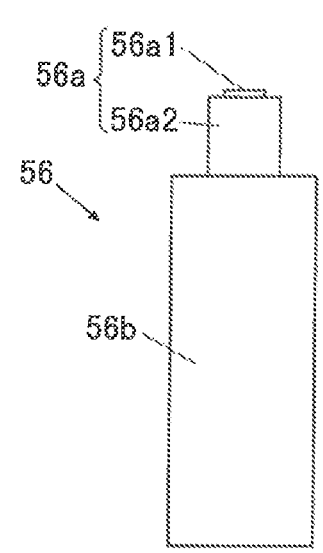
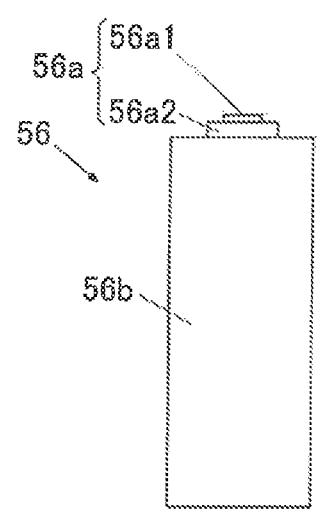
FIG.3
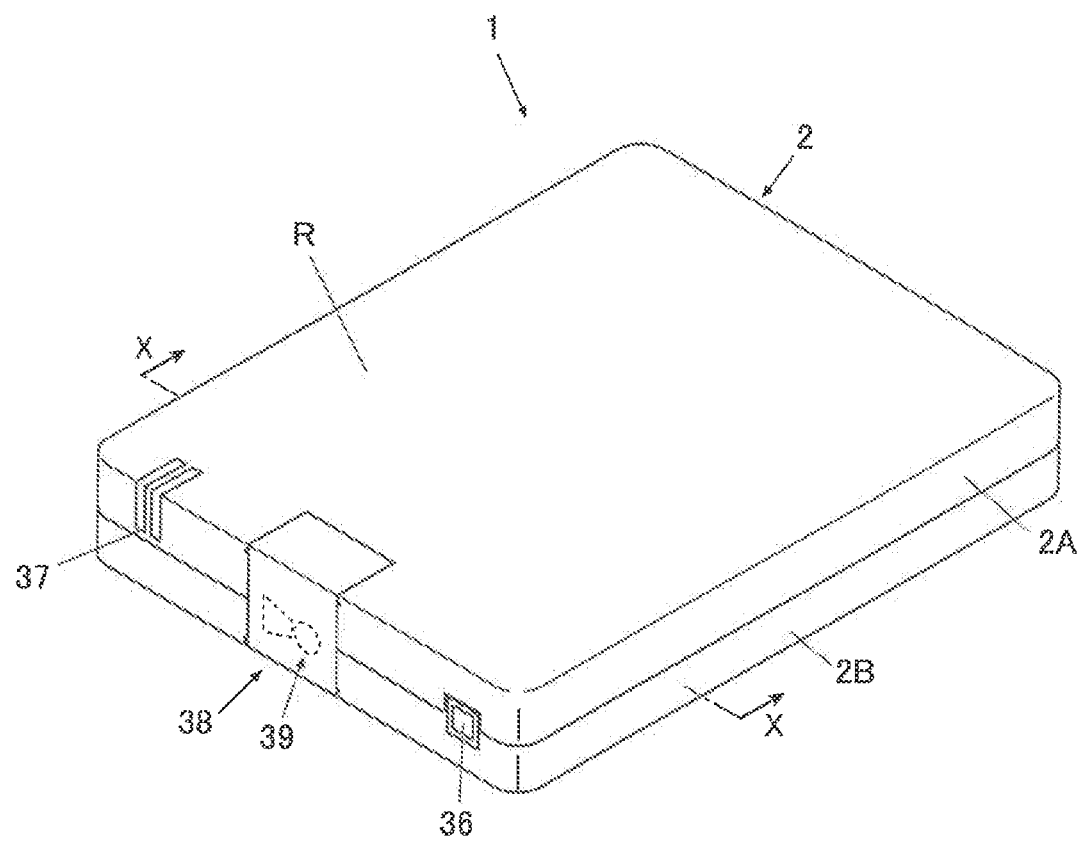

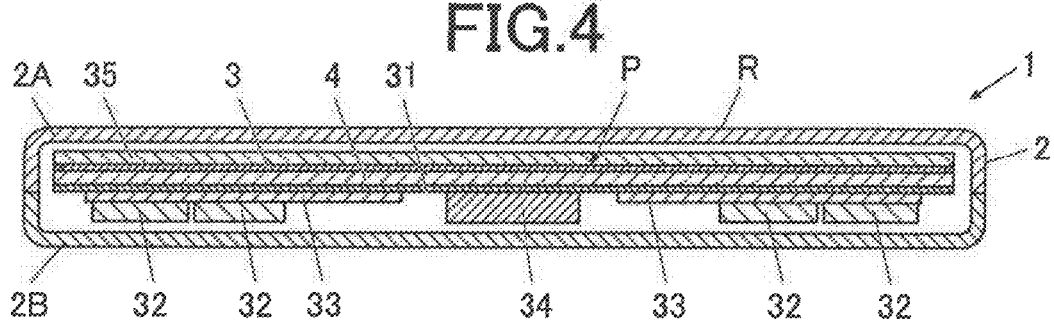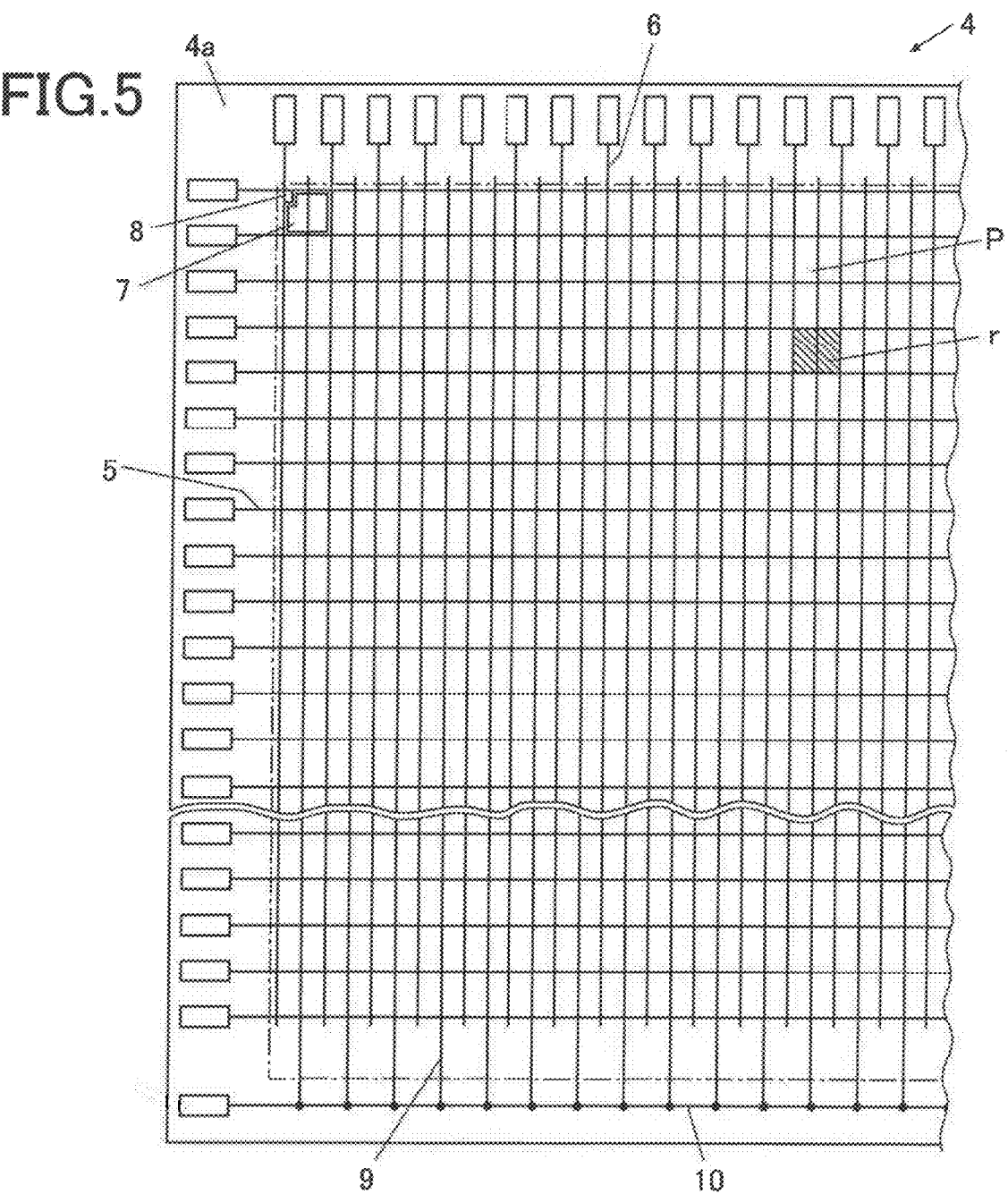

RADIATION IMAGE PHOTOGRAPHING APPARATUS AND RADIATION IMAGE PHOTOGRAPHING SYSTEM FOR RADIATION IMAGE PHOTOGRAPHING PROCESS AND DARK IMAGE ACQUIRING PROCESS

BACKGROUND

1. Technical Field

The present invention relates to a radiation image photographing apparatus and a radiation image photographing system.

2. Description of the Related Art

There have been developed various radiation image photographing apparatuses each of which generates charges in radiation detecting elements depending on the dose of an emitted radiation and each of which includes a radiation detector (FPD: Flat Panel Detector) to read the generated charges as image data (for example, see Japanese Patent Laid-Open No. 2012-84958).

In such a radiation image photographing apparatus, even in a state where radiation irradiation is not performed, a dark charge is generated in each radiation detecting element, due to thermal excitation caused by the heat of the radiation detecting element, and the like, and the charge accumulated in the radiation detecting element, that is, the image data includes an offset quantity (offset signal value) due to the dark charge. Therefore, for acquiring a high-quality radiation image, typically, a dark image acquiring process of reading the data (hereinafter, referred to as "dark image data") of the offset quantity due to the dark charge, from each radiation detecting element, with no radiation irradiation is performed before or after a radiation image photographing process of acquiring the image data of the radiation image by accumulating the charge generated by radiation irradiation in each radiation detecting element and reading the accumulated charge. Then, an offset correction of removing the offset quantity due to the dark charge from the radiation image is performed by subtracting the dark image data from the image data of the radiation image acquired by the radiation image photographing process.

Further, in the radiation image photographing apparatus, for acquiring a high-quality radiation image, a reset process of resetting each radiation detecting element by releasing an excess charge such as the dark charge that is accumulated in each radiation detecting element is performed before the radiation image is photographed, that is, before the charge generated by the radiation irradiation is accumulated in each radiation detecting element.

Specifically, in the reset process, for example, as shown in FIG. 7 described later, an on-voltage is applied from a gate driver 15b of a scan driver 15 to each of lines (gate lines) L1 to Lx of scan lines 5, and each thin film transistor (hereinafter, referred to as a "TFT") 8 that is a switch having a gate electrode 8g (which is denoted by G in the figure) connected with each of the lines L1 to Lx of the scan lines 5 is put into an on-state. Thereby, the excess charge is released from the radiation detecting element 7 to a signal line 6 through the TFT 8. The reset process is performed while the on-voltage is sequentially applied from the gate driver 15b to the lines L1 to Lx of the scan lines 5 and the TFT 8 to be put into the on-state is sequentially switched.

After the reset process, in the case of the radiation image photographing process, by the transition to a charge accumulation mode, the radiation image is photographed, and the charge generated in each radiation detecting element 7 by the radiation irradiation, that is, the image data is accumulated in each radiation detecting element 7. Then, in the subsequent reading process, from each radiation detecting element 7, the excess charge remaining in the radiation detecting element 7 as described above is read together with the proper image data.

Further, after the reset process, in the case of the dark image acquiring process, by the transition to the charge accumulation mode, the charge generated in each radiation detecting element 7 in the state where the radiation irradiation is not performed, that is, the dark image data is accumulated in each radiation detecting element 7. Then, in the subsequent reading process, the dark image data is read from each radiation detecting element 7.

In the meantime, as shown in FIG. 13B, in recent radiation image photographing apparatuses, the line number of the scan lines tends to increase with the increase in the definition of the radiation image, compared to that in conventional apparatuses shown in FIG. 13A. For example, the reset process is started by a predetermined trigger for the start of the photographing, as exemplified by a depression of a first button of an exposure switch by a user, and the reset process is repeated until a depression of a second button that gives an instruction of the radiation irradiation, or the like is performed. When the second button is depressed, at the time when the reset process in execution is completed to the last scan line, the transition to the charge accumulation mode is performed, an interlock is unlocked, and the irradiation (exposure) with a radiation is performed. That is, there is a delay after the depression of the second button and before the start of the exposure. When the line number of the scan lines increases with the increase in the definition, the reset time (the time after the start of the reset of the line L1 and before the completion of the reset of the last line Lx) increases, and thereby, the maximum exposure delay time increases, as shown in FIG. 13B. However, it is preferable that the time after the user depresses the second button to gives an instruction of the exposure and before the exposure is actually started is as short as possible, in consideration of usability. Therefore, in the radiation image photographing apparatus with a high definition, the reset time is shortened. With the shortening of the reset time, the reset cycle (the time interval of resets of an identical gate line) is also shortened.

However, when the reset time is shortened, the number (referred to as the continuous reset number) of times of the reset process that is continuously performed before the radiation exposure increases as the time after the depression of the first button and before the depression of the second button increases. Thereby, a gap is generated between the offset signal value included in the image data of the radiation image and the offset signal value indicated by the dark image data.

It is known that the offset signal value is influenced by two types of variation factors. As one variation factor, the offset signal value decreases due to the release of the charge accumulated in the radiation detecting element. As the other variation factor, it is known that when the TFT is turned on, the offset signal value rapidly increases, and when the TFT is turned off, the offset signal value gradually decreases and then becomes constant. FIG. 14A is a graph showing a temporal change in offset signal value associated with the on/off switching of TFTs in a radiation image photographing apparatus with a long reset cycle. FIG. 14B is a graph showing a temporal change in offset signal value associated with the on/off switching of the TFTs in a radiation image photographing apparatus with a short reset cycle. As an example, FIG. 14A and FIG. 14B show the offset signal value of the radiation detecting element on the first scan line. As shown in FIG. 14A, in the radiation image photographing apparatus with a long reset cycle, after the offset signal value increased once by the turn-on of the TFTs is sufficiently decreased, the next reset process can be performed, in the radiation image photographing process. Therefore, there is hardly difference between the offset signal value included in the radiation image and the offset signal value of the dark image data. However, as shown in FIG. 14B, in the case where the reset cycle is short, before the offset signal value increased once by the turn-on of the TFTs in the reset process is sufficiently decreased, the offset signal value is increased by the turn-on of the TFTs in the next reset process, in the radiation image photographing process. As the reset time becomes shorter or as the time after the depression of the first button and before the depression of the second button becomes longer, the continuous reset number increases, so that the cumulative increase in offset signal value in the radiation detecting element is repeated. On the other hand, in the dark image acquiring process, only a predetermined number of reset process (for example, one reset process) is performed. Therefore, a gap is generated between the offset signal value included in the image data of the radiation image and the offset signal value of the dark image data, and the offset correction cannot be accurately performed.

For example, the continuous reset number is determined by the time between the depression of the first button of the exposure switch of the radiation generating apparatus and the depression of the second button, and the time varies depending on the using method by the user (it is not possible to know when the user will depress the second button). Therefore, the problem cannot be solved, for example, by the application of a fixed correction to the data of the dark image.

SUMMARY

The present invention has an object to suppress the gap between the offset signal value included in the image data of the radiation image and the offset signal value of the dark image data.

To achieve the abovementioned object, a radiation image photographing apparatus according to an aspect of the present invention includes:
 a plurality of scan lines and a plurality of signal lines that are arranged so as to intersect each other;
 a plurality of radiation detecting elements that is two-dimensionally arrayed in regions separated by the plurality of scan lines and the plurality of signal lines;
 a switch that is disposed for each of the radiation detecting elements, the switch being put into an off-state when an off-voltage is applied to the scan line connected with the switch, the switch being put into an on-state when an on-voltage is applied to the scan line connected with the switch, the switch causing a charge generated in the radiation detecting element to be accumulated in the radiation detecting element in the off-state, the switch causing the charge to be released from the radiation detecting element to the signal line in the on-state;
 a scan driver that switches a voltage to be applied to the scan line, between the on-voltage and the off-voltage;
 a reading circuit that performs an image data reading process of reading image data from the radiation detecting element by converting the charge released from the radiation detecting element into the image data; and
 a hardware processor that performs a radiation image photographing process and a dark image acquiring process by controlling at least the scan driver and the reading circuit, in which
 at a time of the radiation image photographing process, the hardware processor repeats a reset process of releasing the charge from the radiation detecting element and resetting the radiation detecting element by sequentially applying the on-voltage from the scan driver to the plurality of scan lines, until a radiation irradiation is started, provides a predetermined waiting time to cause all the switches to wait in the off-state after the reset process is ended and before the next reset process is started, transitions to a charge accumulation mode of accumulating the charge in the radiation detecting element by applying the off-voltage from the scan driver to all the scan lines, in response to the start of the radiation irradiation, and transitions to a reading mode of releasing the charge from the radiation detecting element by applying the on-voltage from the scan driver to the scan lines, and performing the image data reading process by converting the charge released to the reading circuit into the image data, when a predetermined accumulation time has elapsed, and
 at a time of the dark image acquiring process,
 the hardware processor transitions to the charge accumulation mode to wait in a state where the radiation irradiation is not performed, after the reset process is performed, and transitions to the reading mode when a predetermined time has elapsed.

A radiation image photographing system according to an aspect of the present invention includes: the radiation image photographing apparatus according to claim 1; and a radiation generating apparatus that irradiates the radiation image photographing apparatus with a radiation.

BRIEF DESCRIPTION OF THE DRAWINGS

The objects, advantages and features of the above present invention will become more fully understood from the detailed description given hereinbelow and the appended drawings, and they are not intended to limit the present invention, wherein:

FIG. 1 is a diagram showing the overall configuration of a radiation image photographing system according to an embodiment;

FIG. 2A is a diagram showing the configuration of an exposure switch;

FIG. 2B is a diagram for describing a state where a button part of the exposure switch is half pushed;

FIG. 2C is a diagram for describing a state where the button part of the exposure switch is fully pushed;

FIG. 3 is a perspective view showing a radiation image photographing apparatus according to the embodiment;

FIG. 4 is a cross-section view taken along line X-X in FIG. 3;

FIG. 5 is a plan view showing the configuration of a substrate of the radiation image photographing apparatus;

DETAILED DESCRIPTION OF EMBODIMENTS

Figure 6:
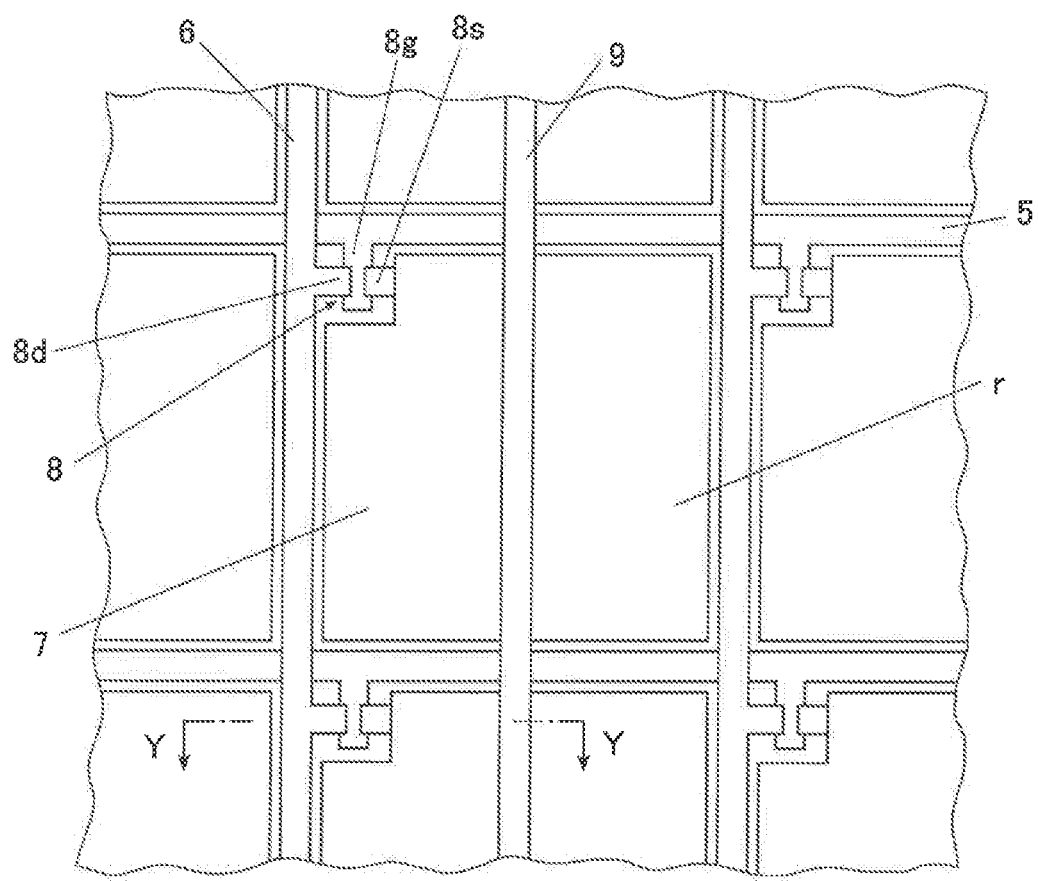
FIG. 6 is an enlarged view showing the configuration of a radiation detecting element, a TFT and the like that are formed in a small region on the substrate in FIG. 5.

Hereinafter, embodiments of the present invention will be described with reference to the drawings. However, the scope of the invention is not limited to the illustrated examples.

Hereinafter, descriptions will be made for the case where a radiation image photographing apparatus is a so-called indirect radiation image photographing apparatus that includes a scintillator and acquires an electric signal by converting an emitted radiation into an electromagnetic wave with a different wavelength such as a visible light. However, the present invention can be applied also to a direct radiation image photographing apparatus. Further, descriptions will be made for the case of a portable radiation image photographing apparatus. However, the present invention can be applied also to a radiation image photographing apparatus that is formed integrally with a support and the like.

[Radiation Image Photographing System]

FIG. 1 is a diagram showing the overall configuration of a radiation image photographing system 50 according to an embodiment.

For example, as shown in FIG. 1, the radiation image photographing system 50 is provided with a photographing room R1 where a subject that is a part of the body of an unillustrated patient (a photographing object site of the patient) is irradiated with a radiation and is photographed, a front room R2 that is adjacent to the photographing room R1 and where an operator (user) such as a radiographer performs various operations such as a control for the start of the irradiation of the subject with the radiation, and an area outside them.

Specifically, as shown in FIG. 1, the radiation image photographing system 50 is configured to include a radiation image photographing apparatus 1 that performs a radiation image photographing process, a console 58 that performs a predetermined image process to the image data of the radiation image photographed by the radiation image photographing apparatus 1, a radiation generating apparatus 55 that irradiates the radiation image photographing apparatus 1 with the radiation, and the like.

For example, the photographing room R1 includes a bucky apparatus 51 that allows the radiation image photographing apparatus 1 to be loaded, a radiation source 52 that includes an X-ray tube (not illustrated) to generate the radiation with which the subject is irradiated, the radiation generating apparatus 55 that controls the radiation source 52, and a radio antenna 53, and there is provided a repeater 54 that relays the communication between the radiation image photographing apparatus 1 and another apparatus such as the console 58 and the radiation generating apparatus 55.

FIG. 1 shows a case where the portable radiation image photographing apparatus 1 is used while being loaded into a cassette holder 51a of the bucky apparatus 51, a case where the radiation image photographing apparatus 1 is used alone without being loaded into the bucky apparatus 51, specifically, a case where the radiation image photographing apparatus 1 is disposed on the upper surface side of a bucky apparatus 51B for recumbent position photographing and the hand or the like of the patient that is the subject is placed on a radiation incidence surface R (see FIG. 3) thereof, and the like. However, the radiation image photographing apparatus 1 may be formed integrally with the bucky apparatus 51, the support and the like.

Here, when the portable radiation image photographing apparatus 1 is used alone without being loaded into the bucky apparatus 51, in addition to the case where the radiation image photographing apparatus 1 is disposed on the upper surface side of the bucky apparatus 51B for recumbent position photographing and the hand or the like of the patient that is the subject is placed on the radiation incidence surface R (see FIG. 3), for example, the radiation image photographing apparatus 1 may disposed on the upper surface side of a bed or the like provided in the photographing room R1 and the hand or the like of the patient that is the subject may be placed on the radiation incidence surface R (see FIG. 3), or for example, the radiation image photographing apparatus 1 may be used while being inserted between the waist, leg or the like of the recumbent patient on the bed and the bed.

The repeater 54 is connected by wire with the console 58 and the radiation generating apparatus 55 through a LAN (Local Area Network) cable or the like. The repeater 54 incorporates a converter (not illustrated) that converts a LAN communication signal or the like for sending information with the radiation image photographing apparatus 1, the console 58 or the like, into a signal for sending information to the radiation generating apparatus 55, and that performs the inverse conversion.

The repeater 54 is connected by wire with the bucky apparatus 51, and the communication between the radiation image photographing apparatus 1 loaded into the bucky apparatus 51 and another apparatus such as the console 58 and the radiation generating apparatus 55 can be performed through the repeater 54 in a wired system.

FIG. 1 shows a configuration in which the radiation image photographing apparatus 1, specifically, the radiation image photographing apparatus 1 not loaded into the bucky apparatus 51 is wirelessly connected with the repeater 54 and the communication between the radiation image photographing apparatus 1 and another apparatus such as the console 58, the radiation generating apparatus 55 can be performed through the repeater 54 in a wireless system. However, it is allowable to adopt a configuration in which the radiation image photographing apparatus 1 and the repeater 54 are connected by wire and the communication between the radiation image photographing apparatus 1 and another apparatus can be performed through the repeater 54 in a wired system.

The radiation image photographing apparatus 1 may be configured to be capable of being wirelessly connected with the repeater 54 even in a state where the radiation image photographing apparatus 1 is loaded into the bucky apparatus 51.

FIG. 1 shows a case where one bucky apparatus 51A for stereography and one bucky apparatus 51B for recumbent position photographing are provided as the bucky apparatus 51 in the photographing room R1. However, the number and type of the bucky apparatus 51 to be provided in the photographing room R1 are not particularly limited.

Further, FIG. 1 shows a case where one radiation source 52A for the bucky apparatus 51 and one portable radiation source 52B are provided as the radiation source 52 in the photographing room R1. However, the number and type of the radiation source 52 to be provided in the photographing room R1 are not particularly limited.

[Radiation Generating Apparatus]

In the photographing room R1, there is provided the radiation generating apparatus 55 that irradiates the radiation image photographing apparatus 1 with the radiation.

In the embodiment, in the front room R2 adjacent to the photographing room R1, there is provided an operation station 57 for the radiation generating apparatus 55, and on the operation station 57, there is provided an exposure switch 56 that is operated when the user such as a radiographer gives instructions of the start of the radiation irradiation and the like, to the radiation generating apparatus 55.

For example, as shown in FIG. 2A, the exposure switch 56 is constituted by a rod-like button part 56a that has a predetermined length of stroke and a housing part 56b that supports the rod-like button part 56a such that the rod-like button part 56a can move in a stroke direction indicated by the arrow S in the figure. For example, the rod-like button part 56a of the exposure switch 56 is configured to include a second button 56a2 that protrudes upward from the housing part 56b and a first button 56a1 that further protrudes upward from the interior. The first button 56a1 is a button for giving an instruction of a standby for the start of the photographing from the user to the radiation image photographing system 50. The second button 56a2 is a button for giving an instruction of the start of the irradiation (exposure) with the radiation from the user to the radiation image photographing system 50.

The exposure switch 56 is configured to send a start-up signal to the radiation generating apparatus 55 through the operation station 57 when the first button 56a1 is pushed to an upper end portion of the second button 56a2 in the stroke direction S as shown in FIG. 2B (that is, when a so-called half-push operation is performed).

The radiation generating apparatus 55 is configured to put the radiation source 52 into a standby state by the start of the rotation of an anode of the X-ray tube of the radiation source 52 and the like, when the radiation generating apparatus 55 receives the start-up signal. Further, the radiation generating apparatus 55 is configured to send a depression notice signal for the first button 56a1 to the radiation image photographing apparatus 1 through the repeater 54.

Furthermore, the exposure switch 56 is configured to send a radiation irradiation start signal to the radiation generating apparatus 55 through the operation station 57 when both of the first button 56a1 and second button 56a2 of the exposure switch 56 are pushed to an upper end portion of the housing part 56b as shown in FIG. 2C (that is, when a so-called full-push operation is performed).

The radiation generating apparatus 55 is configured to send a depression notice signal for the second button 56a2 to the radiation image photographing apparatus 1 through the repeater 54, when the radiation generating apparatus 55 receives the radiation irradiation start signal from the exposure switch 56. When the depression notice signal for the second button 56a2 is received and preparations such as the completion of reset are finished, the radiation image photographing apparatus 1 sends an interlock unlock signal to the radiation generating apparatus 55 through the repeater 54. The radiation generating apparatus 55 is configured to emit the radiation from the X-ray tube of the radiation source 52, when the radiation generating apparatus 55 receives the interlock unlock signal sent from the radiation image photographing apparatus 1 through the repeater 54.

The radiation generating apparatus 55 is configured to allow the user to perform, for example through the operation of the operation station 57, various controls to the radiation source 52, for example, to allow the user to adjust the position of the radiation source 52 and the radiation irradiation direction such that the radiation image photographing apparatus 1 is appropriately irradiated with the radiation, adjust a diaphragm of the radiation source 52 such that a predetermined region of the radiation image photographing apparatus 1 is irradiated with the radiation, or adjust the radiation source 52 such that the irradiation is performed with an appropriate dose of radiation. The radiation generating apparatus 55 may be configured such that the user manually performs these processes.

The radiation generating apparatus 55 is configured to stop the irradiation with the radiation from the radiation source 52, for example, by stopping the X-ray tube of the radiation source 52, at the time when a predetermined time has elapsed since the start of the irradiation with the radiation from the radiation source 52, or at the time when a radiation irradiation end signal has been sent from the radiation image photographing apparatus 1. Here, for example, the predetermined time is a radiation irradiation time that is previously determined by the user before the radiation image photographing, a radiation irradiation time corresponding to a photographing condition menu such as the photographing object site and the photographing direction that is previously determined by the user before the radiation image photographing, or the like.

[Console]

For example, as shown in FIG. 1, the console 58 is a computer configured to include a display device 58a constituted by a CRT (Cathode Ray Tube), a LCD (Liquid Crystal Display) and the like, a storage 59 constituted by a HDD (Hard Disk Drive) and the like, a controller 58b that controls the operation of each device of the console 58, and the like, a communicator 58c that is connected with the repeater 54 through the LAN cable or the like and that performs the communication with another apparatus such as the radiation image photographing apparatus 1, and an input device 60 constituted by a keyboard, a mouse or the like.

FIG. 1 shows a case where the console 58 is provided outside the photographing room R1 and the front room R2. However, the console 58 may be provided in the front room R2, for example.

FIG. 1 shows a case where the storage 59 is connected with the console 58. However, the storage 59 may be incorporated in the console 58.

When the communicator 58c receives the image data of the radiation image photographed by the radiation image photographing apparatus 1 from the radiation image photographing apparatus 1 through the repeater 54, the controller 58b of the console 58 performs, to the image data, predetermined image processes such as an extension process, an offset correction process, a gain correction process and an automatic gradation process, and creates image data for diagnosis.

Then, in accordance with an instruction from the input device 60 or the like operated by the user, the controller 58b of the console 58 displays a radiation image based on the image data for diagnosis, on the display device 58a, or outputs the image data for diagnosis from the communicator 58c or the like and sends the image data for diagnosis to another apparatus (not illustrated) such as an imager or a data management server.

In the embodiment, descriptions will be made for the case where the offset correction process, the gain correction process, the automatic gradation process and the like are performed by the console 58. However, the offset correction process, the gain correction process, the automatic gradation process and the like may be performed by the radiation image photographing apparatus 1.

The console 58 is configured when appropriate, and for example, can be configured to display a preview image based on the image data acquired by the radiation image photographing, to have a function to switch the drive mode of the radiation image photographing apparatus 1 between a wake mode and a sleep mode, or to have a function to allow the user to create or select photographing order information indicating the content of the radiation image photographing that is performed in the photographing room R1.

[Radiation Image Photographing Apparatus]

FIG. 3 is an external perspective view of the radiation image photographing apparatus 1 according to the embodiment, and FIG. 4 is a cross-sectional view taken along line X-X in FIG. 3.

As shown in FIG. 3 and FIG. 4, the radiation image photographing apparatus 1 according to the embodiment is configured as a portable (cassette type) apparatus in which a scintillator 3, a substrate 4 and the like are contained within a housing 2.

In the housing 2, at least a surface R (referred to as a "radiation incidence surface R") that is irradiated with the radiation is formed of a material such as a carbon plate or a plastic that transmits the radiation.

FIG. 3 and FIG. 4 show a case where the housing 2 is a so-called lunchbox type formed by a frame plate 2A and a back plate 2B. However, the housing 2 may be a so-called monocoque type integrally formed in a square tube shape.

As shown in FIG. 3, in the embodiment, a power supply switch 36, an indicator 37 constituted by an LED or the like, a lid member 38 configured to be capable of being opened and closed for the replacement of a battery 41 (see FIG. 7 described later), and the like are disposed on a side portion of the housing 2. Further, in the embodiment, an antenna apparatus 39 is buried in the side portion of the lid member 38.

Here, the antenna apparatus 39 functions as a communication device for performing the sending and receiving of information such as data and signals with another apparatus such as the console 58 and the radiation generating apparatus 55 through the repeater 54, in a wireless system.

In the case where the communication between the radiation image photographing apparatus 1 and another apparatus is performed in a wired system described above, a connector for connecting the LAN cable or the like is provided as a communication device, in the radiation image photographing apparatus 1.

In the interior of the housing 2, as shown in FIG. 4, a base 31 is disposed on the lower side of the substrate 4, with an unillustrated lead thin plate composed or the like therebetween, and a PCB substrate 33 provided with electronic components 32 and others, a buffer member 34 and the like are attached to the base 31. In the embodiment, a glass substrate 35 for protecting the substrate 4 and the scintillator 3 is provided on the side of the radiation incidence surface R of the substrate 4 and the scintillator 3.

The scintillator 3 is disposed so as to face a later-described detection part P of the substrate 4. As the scintillator 3, for example, there is used a scintillator that is principally composed of a fluorescent material and that, when receiving the radiation, converts the radiation into electromagnetic waves with wavelengths of 300 to 800 nm, that is, electromagnetic waves mainly including visible lights, to output the electromagnetic waves.

In the embodiment, the substrate 4 is composed of a glass substrate 35, and as shown in FIG. 5, a plurality of scan lines 5 and a plurality of signal lines 6 are arranged so as to intersect each other, on a surface 4a that faces the scintillator 3 of the substrate 4. A plurality of radiation detecting elements 7 are respectively provided in regions r separated by the plurality of scan lines 5 and the plurality of signal lines 6 on the surface 4a of the substrate 4.

Thus, the detection part P is the whole of regions r where the plurality of radiation detecting elements 7 two-dimensionally arrayed in the regions r separated by the plurality of scan lines 5 and the plurality of signal lines 6 are provided, that is, the region indicated by the chain line in FIG. 5.

In the embodiment, as the plurality of radiation detecting element 7, a photodiode is used. However, other than the photodiode, for example, a phototransistor or the like can be used.

As shown in FIG. 5 and FIG. 6, which is an enlarged view of FIG. 5, each radiation detecting element 7 is connected with a source electrode 8s of a TFT 8 that is a switch. Further, a drain electrode 8d of the TFT 8 is connected with the signal line 6.

When an on-voltage is applied to the scan line 5 connected with the TFT 8 by a later-described scan driver 15 and the on-voltage is applied to a gate electrode 8g through the scan line 5, the TFT 8 is put into an on-state, so that the charge accumulated in the radiation detecting element 7 is released from the radiation detecting element 7 to the signal line 6.

When an off-voltage is applied to the scan line 5 connected with the TFT 8 and the off-voltage is applied to the gate electrode 8g through the scan line 5, the TFT 8 is put into an off-state, so that the release of the charge from the radiation detecting element 7 to the signal line 6 is stopped and the charge generated in the radiation detecting element 7 is held and accumulated in the radiation detecting element 7.

Figure 7:
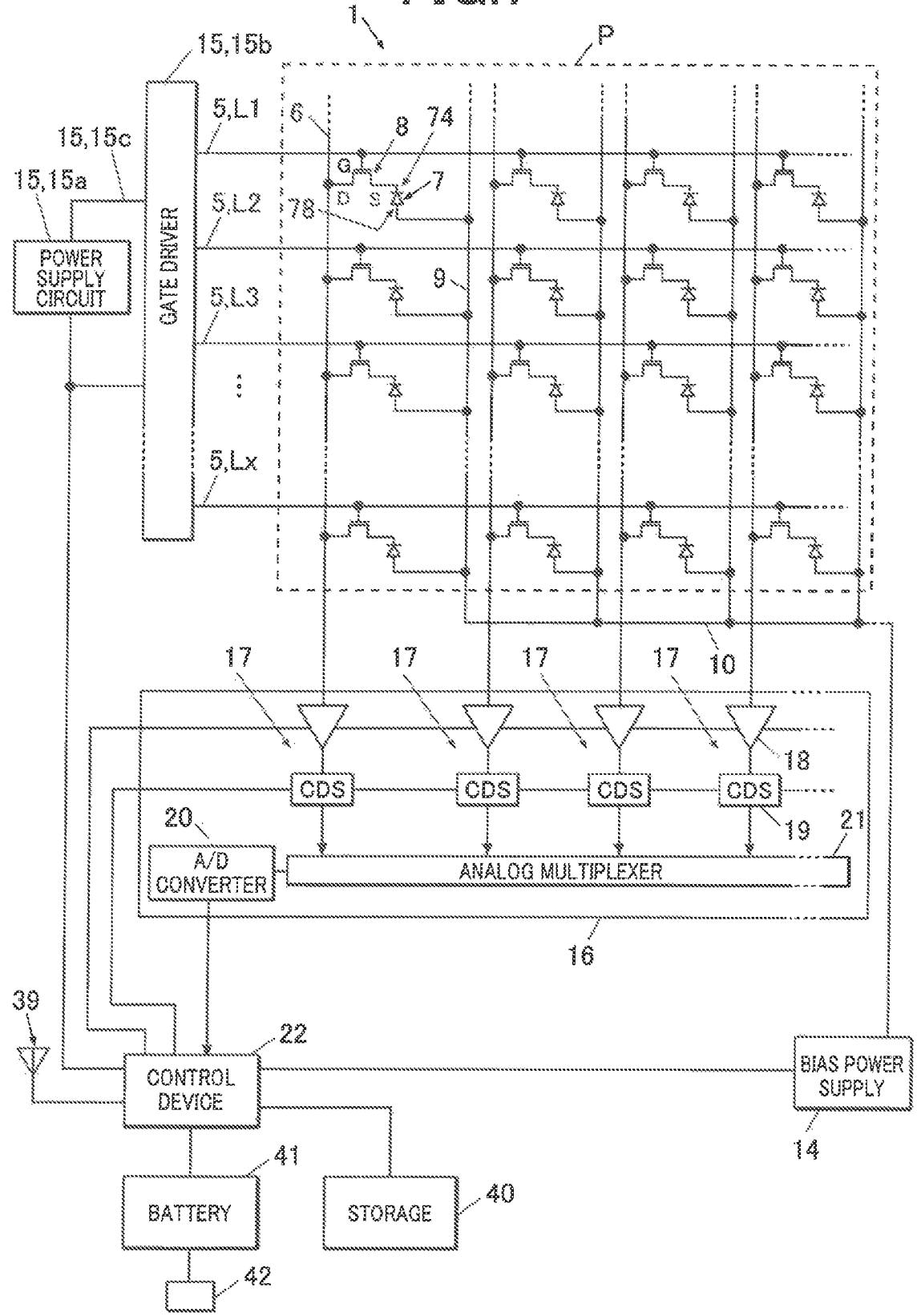
FIG. 7 is a block diagram illustrating an equivalent circuit of a radiation image photographing apparatus.
Figure 8:
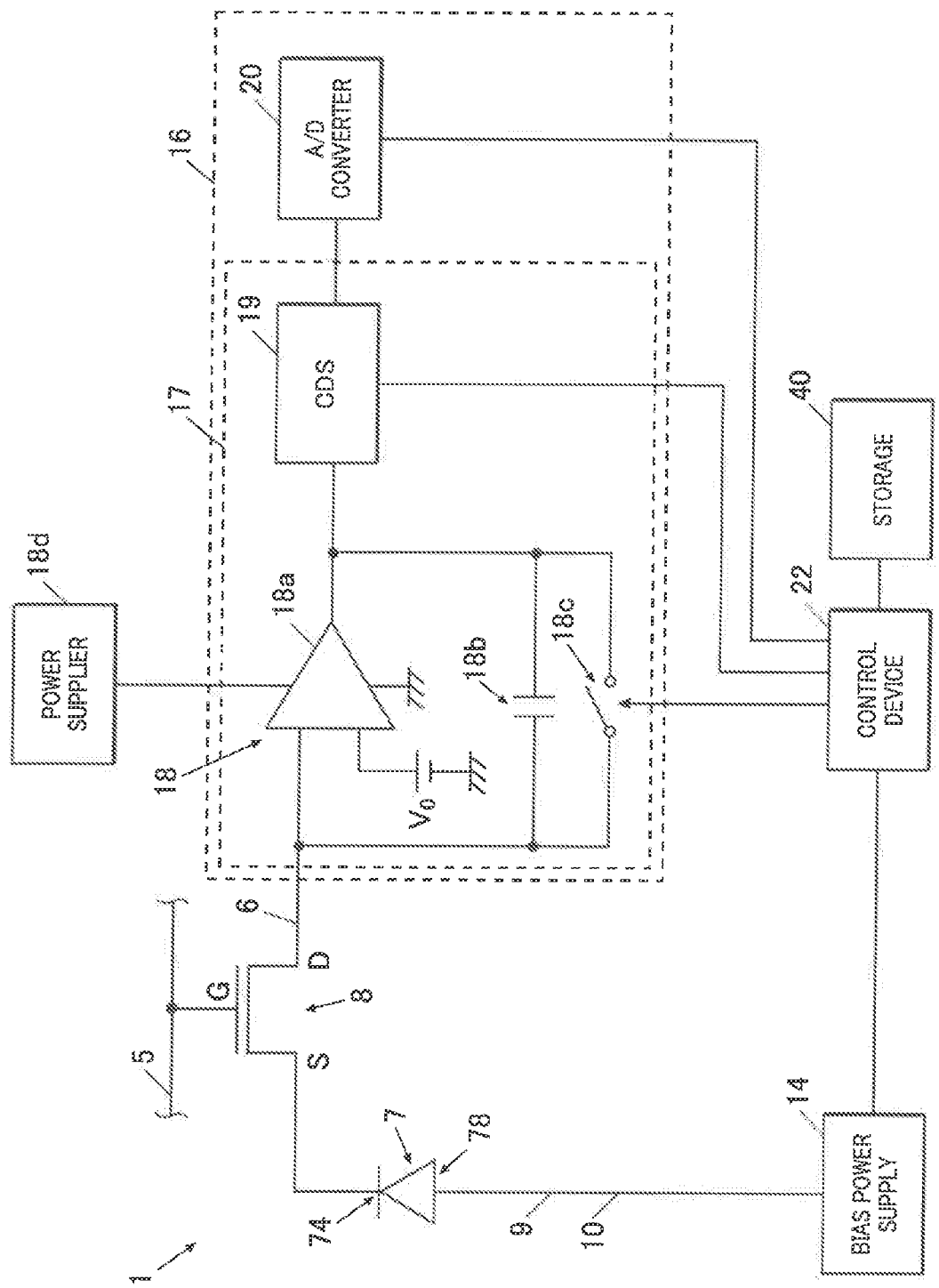
FIG. 8 is a block diagram illustrating an equivalent circuit corresponding to one of pixels that constitute a detection part.

Here, the circuit configuration of the radiation image photographing apparatus 1 will be described. FIG. 7 is a block diagram illustrating an equivalent circuit of the radiation image photographing apparatus 1 according to the embodiment, and FIG. 8 is a block diagram illustrating an equivalent circuit corresponding to one of pixels that constitute the detection part P.

Bias wires 9 are respectively connected with second electrodes 78 of the radiation detecting elements 7 of the detection part P of the substrate 4, and the bias wires 9 are bound by a connecting wire 10 and are connected with a bias power supply 14. The bias power supply 14 applies a bias voltage to the second electrodes 78 of the radiation detecting elements 7 through the connecting wire 10 and the bias wires 9, respectively.

The bias power supply 14 is connected with a later-described control device 22, and the bias voltage to be applied from the bias power supply 14 to the radiation detecting elements 7 is controlled by the control device 22.

In the embodiment, as the bias voltage, a voltage equal to or lower than a voltage to be applied to a first electrode 74 side of the radiation detecting element 7 (that is, a so-called reverse bias voltage) is applied from the bias power supply 14 to the second electrode 78 of the radiation detecting element 7 through the bias wire 9.

The first electrodes 74 of the radiation detecting elements 7 are connected with the source electrodes 8s (which are denoted by S in FIG. 7 and FIG. 8) of the TFTs 8, and the gate electrodes 8g (which are denoted by G in FIG. 7 and FIG. 8) of the TFTs 8 are respectively connected with lines L1 to Lx of the scan lines 5 that extend from the gate driver 15b of the scan driver 15 described later. The drain electrodes 8d (which are denoted by D in FIG. 7 and FIG. 8) of the TFTs 8 are respectively connected with the signal lines 6.

The scan driver 15 includes a power supply circuit 15a that supplies the on-voltage and the off-voltage to the gate driver 15b through a wire 15c, and the gate driver 15b that switches the TFTs 8 between the on-state and the off-state by switching the voltage to be applied to the lines L1 to Lx of the scan lines 5 between the on-voltage and the off-voltage.

As shown in FIG. 7 and FIG. 8, the signal lines 6 are respectively connected with reading circuits 17 formed in a reading IC 16. In the embodiment, one reading circuit 17 is provided for each signal line 6, in the reading IC 16.

The reading circuit 17 is constituted by an amplifier circuit 18, a correlated double sampling (CDS) circuit 19 and the like. In the reading IC 16, an analog multiplexer 21 and an A/D converter 20 are further provided. In FIG. 7 and FIG. 8, the correlated double sampling circuit 19 is denoted by CDS. In FIG. 8, the analog multiplexer 21 is omitted.

In the embodiment, the amplifier circuit 18 is constituted by a charge amplifier circuit, and is configured to include an operational amplifier 18a, and a capacitor 18b and a charge reset switch 18c that are connected in parallel with the operational amplifier 18a. Further, the amplifier circuit 18 is connected with a power supplier 18d for supplying power to the amplifier circuit 18.

The signal line 6 is connected with the inverting input terminal of the input side of the operational amplifier 18a of the amplifier circuit 18, and a reference potential V0 is applied to the non-inverting input terminal on the input side of the operational amplifier 18a of the amplifier circuit 18.

The reference potential V0 is set to an appropriate value, and in the embodiment, for example, 0 [V] is applied.

The charge reset switch 18c of the amplifier circuit 18 is connected with the control device 22, and the on/off is controlled by the control device 22.

When the TFT 8 is put into the on-state while the charge reset switch 18c is in the off-state (that is, the on-voltage is applied to the gate electrode 8g of the TFT 8 through the scan line 5), the accumulated charge from the radiation detecting element 7 through the TFT 8 in the on-state is released to the signal line 6. The charge flows through the signal line 6, and flows into the capacitor 18b of the amplifier circuit 18, to be accumulated.

In the amplifier circuit 18, a voltage value corresponding to the amount of the charge accumulated in the capacitor 18b is output to the output side of the operational amplifier 18a. Thus, the amplifier circuit 18 performs a charge-voltage conversion by outputting the voltage value corresponding to the amount of the charge output from the radiation detecting element 7.

When the amplifier circuit 18 is reset, the charge reset switch 18c is put into the on-state, and the input side and output side of the amplifier circuit 18 are short-circuited, so that the charge accumulated in the capacitor 18b is discharged. Then, the discharged charge passes through the operational amplifier 18a from the output terminal side of the operational amplifier 18a, and flows from the non-inverting input terminal to the earth or flows to the power supplier 18d. Thereby, the amplifier circuit 18 is reset.

The amplifier circuit 18 may be configured to output electric current corresponding to the charge output from the radiation detecting element 7.

The correlated double sampling circuit (CDS) 19 is connected with the output side of the amplifier circuit 18. In the embodiment, the correlated double sampling circuit 19 has a sample and hold function. In the sample and hold function of the correlated double sampling circuit 19, the on/off is controlled by a pulse signal that is sent from the control device 22.

In a reading process of image data from each radiation detecting element 7 after radiation image photographing, the control device 22 controls the amplifier circuit 18 and the correlated double sampling circuit 19, such that the amplifier circuit 18 performs the charge-voltage conversion of the charge released from the radiation detecting element 7 and the correlated double sampling circuit 19 samples the voltage value after the charge-voltage conversion and outputs the voltage value to the downstream side as the image data.

The image data of the radiation detecting elements 7 output from the correlated double sampling circuits 19 is sent to the analog multiplexer 21, and is sequentially sent from the analog multiplexer 21 to the A/D converter 20. Then, the image data is sequentially converted into image data having digital values, by the A/D converter 20, and is sequentially output and saved in a storage 40.

As described later, the control device 22 performs an image data reading process of sequentially switching the lines L1 to Lx of the scan lines 5 to which the on-voltage is applied from the gate driver 15b of the scan driver 15, and reading the image data from the radiation detecting element 7 as described above for each switching.

The control device 22 is constituted by an unillustrated computer in which a CPU (Central Processing Unit), a ROM (Read Only Memory), a RAM (Random Access Memory), an input-output interface and the like are connected with a bus, an unillustrated FPGA (Field Programmable Gate Array), and the like. The control device 22 may be constituted by a dedicated control circuit. The control device 22 controls the operation and the like of each member of the radiation image photographing apparatus 1.

As shown in FIG. 7 and the like, the control device 22 is connected with the storage 40 constituted by a DRAM (Dynamic RAM) and the like.

In the embodiment, the control device 22 is connected with the antenna apparatus 39.

Furthermore, in the embodiment, the control device 22 is connected with the battery 41 for supplying power to function devices such as the detection part P, the scan driver 15, the reading circuit 17, the storage 40 and the bias power supply 14. Further, to the battery 41, a connecting terminal 42 that connects an unillustrated charging apparatus and the battery 41 when power is supplied from the charging apparatus to the battery 41 such that the battery 41 is charged is attached.

The control device 22 controls the operation of each function device of the radiation image photographing apparatus 1, for example, controls the bias power supply 14 to set the bias voltage to be applied from the bias power supply 14 to each radiation detecting element 7, controls the on/off of the charge reset switch 18c of the amplifier circuit 18 of the reading circuit 17, or controls the on/off of the sample and hold function by sending the pulse signal to the correlated double sampling circuit 19.

When the control device 22 receives a depression notice signal for the first button 56a1 from the radiation generating apparatus 55, the control device 22 controls each device to perform a radiation image photographing process, acquires image data of a radiation image of a subject, and then, performs a dark image acquiring process to acquire dark image data.

<Photographing Process and Dark Image Acquiring Process>

In the radiation image photographing process, the control device 22 repeatedly executes the reset process until a depression notice signal for the second button 56a2 from the radiation generating apparatus 55 is received. The reset process is a process of resetting the radiation detecting element 7 while releasing the charge from the radiation detecting element 7 by sequentially applying the on-voltage to the lines L1 to Lx of the scan lines 5 through the gate driver 15b of the scan driver 15. When the depression notice signal for the second button 56a2 is received, the control device 22 completes the reset process in execution to the line Lx. Thereafter, the control device 22 permits the radiation irradiation by sending the interlock unlock signal to the radiation generating apparatus 55, and transitions to a charge accumulation mode of accumulating the charge in the radiation detecting element 7 by applying the off-voltage to all the scan lines 5 through the scan driver 15. When a predetermined accumulation time has elapsed, the control device 22 transitions to a reading mode of releasing the charge from the radiation detecting element 7 by applying the on-voltage from the scan driver 15 to the lines of the scan lines 5, and performing the image data reading process by converting the charge released to the reading circuit 17 into the image data.

In the dark image acquiring process, after a predetermined number of reset processes (in the embodiment, one reset process), the control device 22 transitions to the charge accumulation mode, and waits in a state where the radiation irradiation is not performed. When a predetermined time has elapsed, the control device 22 transitions to the reading mode, and acquires dark image data.

In the reset process, the voltage to be applied to the lines L1 to Lx of the scan lines 5 is switched between the on-voltage and the off-voltage, at the same timing as the timing in the image data reading process of reading the image data from the radiation detecting elements 7.

Figure 14A:
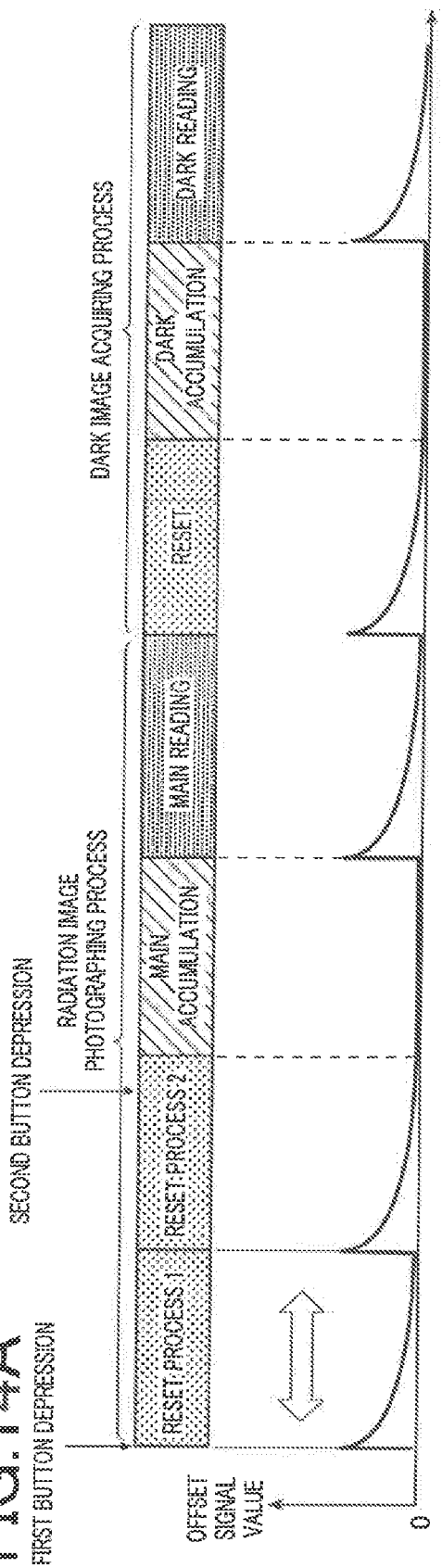
FIG. 14A is a graph showing a temporal change in offset signal value associated with the on/off switching of TFTs in a radiation image photographing apparatus with a long reset cycle.
Figure 14B:
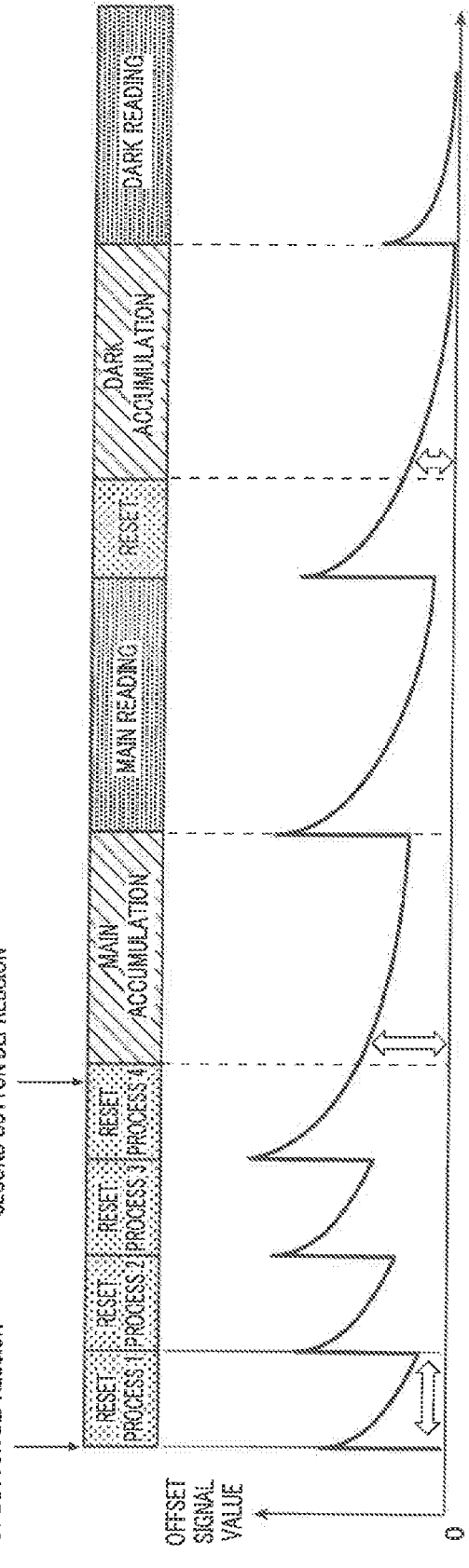
FIG. 14B is a graph showing a temporal change in offset signal value associated with the on/off switching of the TFTs in a radiation image photographing apparatus with a short reset cycle.

Here, the radiation image photographing apparatus 1 in the embodiment is a radiation image photographing apparatus for acquiring a high-definition radiation image, and the line number of the provided scan lines 5 is larger compared to general radiation image photographing apparatuses. For suppressing the increase in the delay time after the user depresses the second button 56a2 and before the radiation irradiation is actually performed, the reset time required for the reset process is set to a shorter time compared to general radiation image photographing apparatuses. However, when the reset time is short, as described above, the continuous reset number increases as the time after the depression of the first button 56a1 and before the depression of the second button 56a2 becomes longer. Therefore, when the reset time and the reset cycle are identical as in the case of the related art, the gap between the signal value corresponding to the offset quantity of the image data of the radiation image and the dark image data becomes large (see FIG. 14B).

Figure 9:
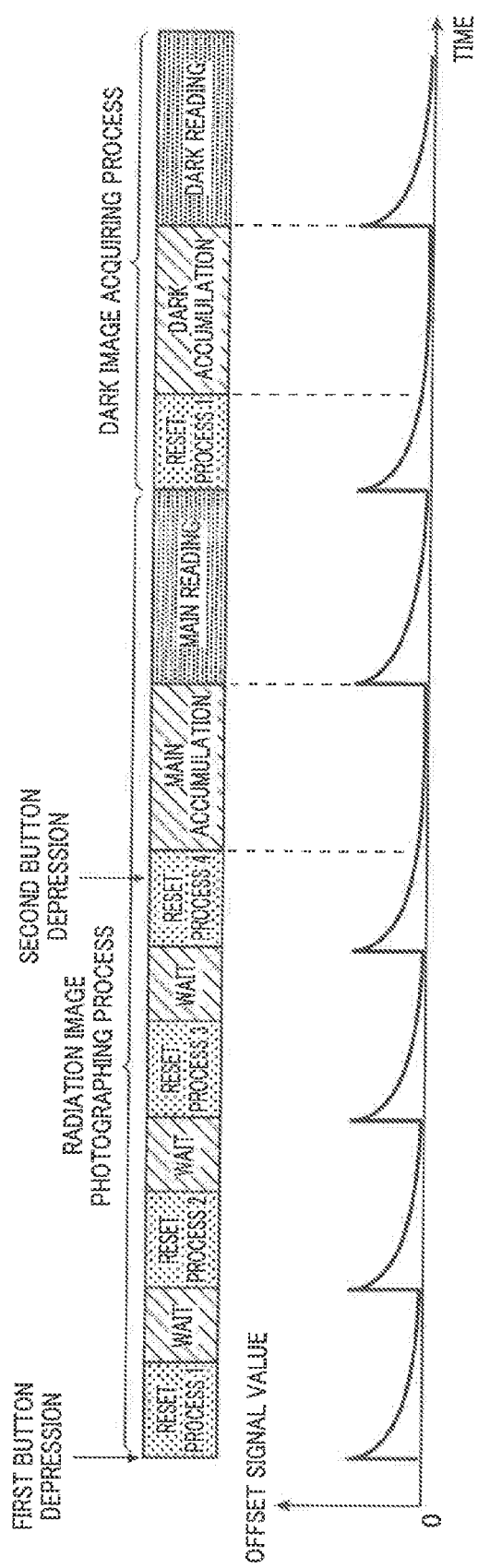
FIG. 9 is a graph showing a temporal change in offset signal value associated with the operation of the radiation detecting element and the on/off switching of TFTs in the embodiment.
Figure 10A:
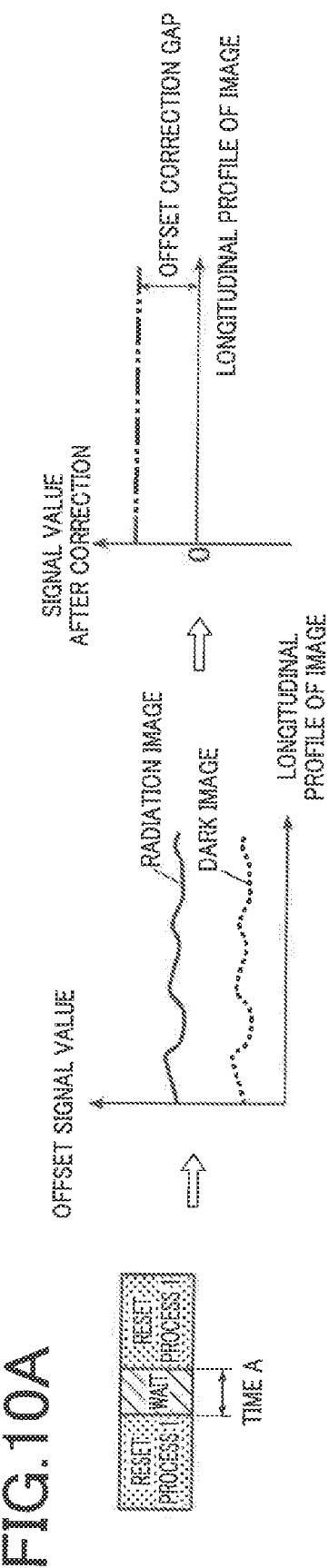
FIG. 10A is a diagram showing the relation in offset signal value between a radiation image and a dark image in the case of a short waiting time.
Figure 10B:
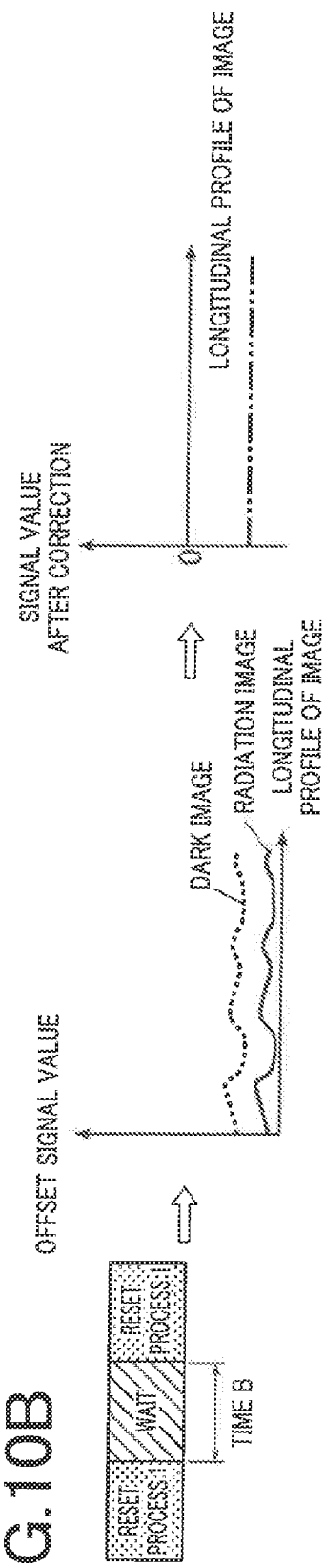
FIG. 10B is a diagram showing the relation in offset signal value between the radiation image and the dark image in the case of a long waiting time.
Figure 10C:
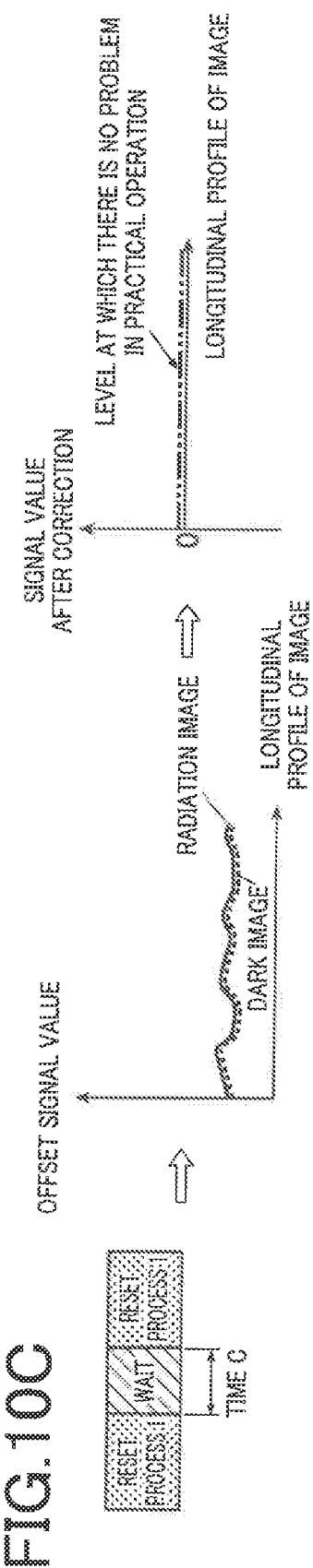
FIG. 10C is a diagram showing the relation in offset signal value between the radiation image and the dark image in the case of an optimal waiting time.

Hence, as shown in FIG. 9, the control device 22, by controlling the scan driver 15, provides a waiting time (waiting mode) to cause all the TFTs 8 in the off-state after the reset process is ended and before the next reset process is started, in the radiation image photographing process, and thereby, prolongs the reset cycle compared to the reset time. Here, as shown in FIG. 10A, when the waiting time is too short, the offset signal value included in the image data of the radiation image is still larger than the offset signal value of the dark image data, and an offset correction gap is generated in the image after the offset correction. As shown in FIG. 10B, when the waiting time is too long, the offset signal value included in the image data of the radiation image is smaller than the offset signal value of the dark image data, and an offset correction gap is generated in the image after the offset correction. Hence, as shown in FIG. 10C, a waiting time by the image after the offset correction becomes an image that is acceptable as a diagnostic image is evaluated by experiments, and the evaluated waiting time is previously set. During the waiting time, all the TFTs 8 only need to wait in the off-state, and devices other than the TFTs 8 may perform other operations.

Figure 11:
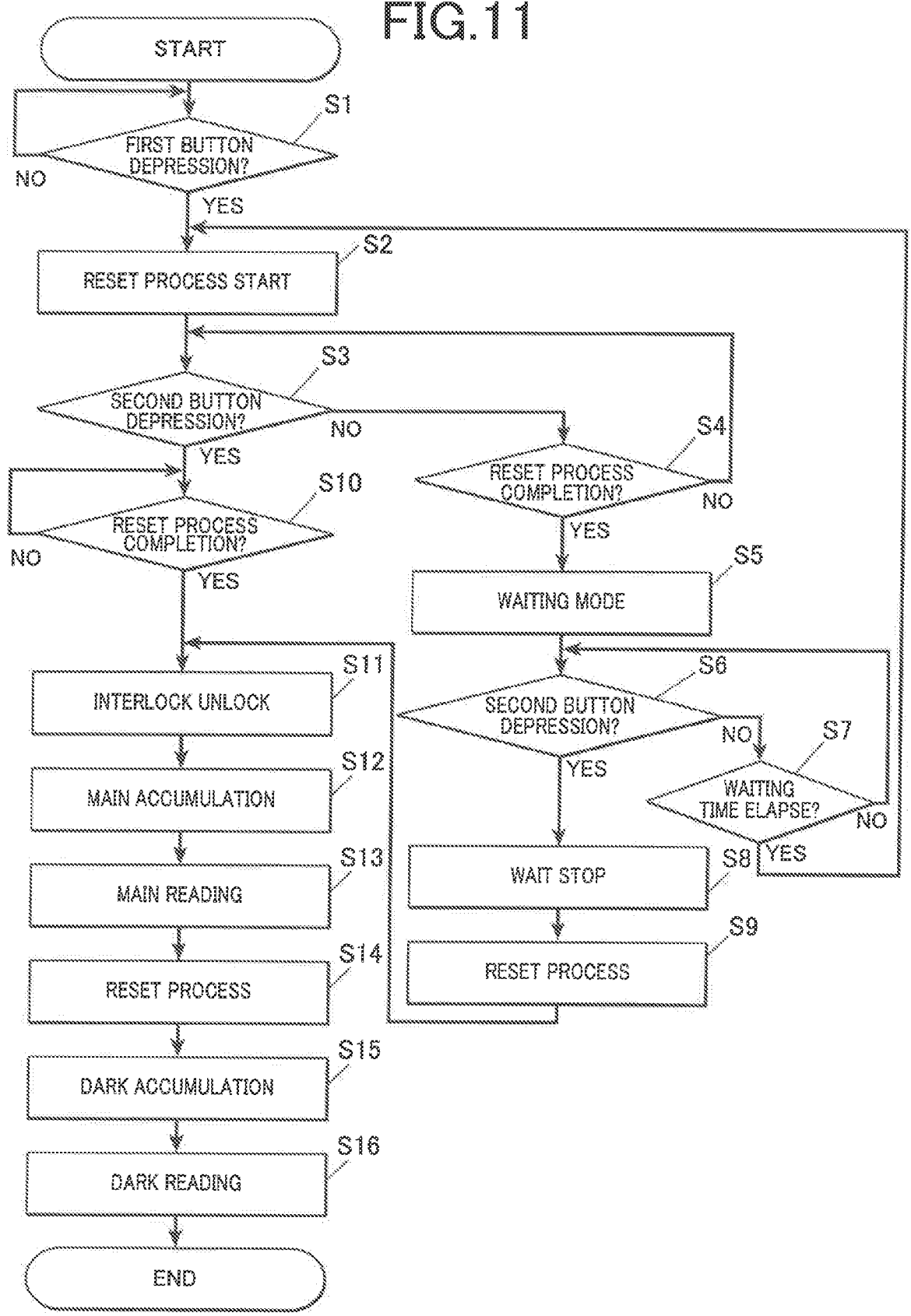
FIG. 11 is a diagram showing a flow of a radiation image photographing process and a dark image acquiring process that are executed by a control device in FIG. 7.

FIG. 11 is a flowchart showing a flow of the radiation image photographing process and dark image acquiring process that are executed by the control device 22. The flow of the radiation image photographing process and dark image acquiring process will be described below, with reference to FIG. 11.

First, the control device 22 waits to receive the depression notice signal for the first button 56a1 from the radiation generating apparatus 55 (step S1). When the depression notice signal for the first button 56a1 is received through the antenna apparatus 39 (step S1; YES), the control device 22 starts the reset process (step S2). That is, the radiation detecting elements 7 are reset while the timing when the on-timing is applied from the gate driver 15b of the scan driver 15 to the lines L1 to Lx of the scan lines 5 is sequentially switched from the line L1 to the line Lx.

Next, the control device 22 judges whether the depression notice signal for the second button 56a2 from the radiation generating apparatus 55 has been received (step S3). In the case where the control device 22 judges that the depression notice signal for the second button 56a2 has not been received (step S3; NO), the control device 22 judges that the reset process has been completed (step S4). In the case where the control device 22 judges that the reset process has not been completed (step S4; NO), the control device 22 returns to step S3.

On the other hand, in the case where the control device 22 judges in step S4 that the reset process has been completed (step S4; YES), the control device 22 transitions to the waiting mode to cause all the lines L1 to Lx of the TFTs 8 in the off-state, through the control of the gate driver 15*b* of the scan driver 15 (step S5).

In the waiting mode, the control device 22 judges whether the depression notice signal for the second button 56*a*2 has been received (step S6).

In the case where the control device 22 judges that the depression notice signal for the second button 56*a*2 has not been received (step S6; NO), the control device 22 judges whether a predetermined waiting time has elapsed (step S7).

In the case where the control device 22 judges that the waiting time has not elapsed (step S7; NO), the control device 22 returns to step S6.

In the case where the control device 22 judges that the depression notice signal for the second button 56*a*2 has been received in the waiting mode (step S6; YES), the control device 22 forcibly stops the waiting mode (step S8), performs a predetermined number of reset processes (in the embodiment, one reset process) (step S9), and transitions to step S11.

The reason why the reset process is executed in step S9 is that the continuous execution of the waiting mode and the charge accumulation mode greatly decreases the offset signal value and causes an unbalance against the dark image data.

When the control device 22 judges that the waiting time has elapsed without the depression of the second button 56*a*2 (step S7; NO), the control device 22 returns to step S2, and performs the reset process again.

In the case where the control device 22 judges that the depression notice signal for the second button 56*a*2 has been received during the reset process (step S3; YES), the control device 22 waits for the completion of the reset process in execution (that is, the reset completion by the application of the on-voltage to the last scan line in the reset process in execution). After the completion of the reset process in execution (step S10; YES), the control device 22 transitions to step S11.

In step S11, the control device 22 sends the interlock unlock signal to the radiation generating apparatus 55 through the antenna apparatus 39 (step S11). Then, the control device 22 transitions to the charge accumulation mode, and accumulates the charge generated in the radiation detecting elements 7 by the radiation irradiation, in the radiation detecting elements 7 (main accumulation) (step S12).

When a predetermined accumulation time has elapsed, the control device 22 transitions to the reading mode, and reads the image data from the radiation detecting elements 7 (main reading) (step S13). Specifically, the control device 22 performs the image data reading process of releasing the charge accumulated in the radiation detecting elements 7 from the radiation detecting elements 7 to the signal lines 6 by applying the on-voltage from the scan driver 15 to the scan lines 5, and reading the image data from the radiation detecting elements 7 by converting the charge released to the reading circuits 17 into the image data.

In the process of step S1 to step S13, which is the radiation image photographing process, the image data of the radiation image of the subject is acquired.

When the image data reading process is ended, the control device 22 performs a predetermined number of reset processes (in the embodiment, one reset process) (step S14). When the predetermined number of reset processes is ended, the control device 22 transitions to the charge accumulation mode, and performs the dark accumulation by waiting for a predetermined time in a state where the radiation image photographing apparatus 1 is not irradiated with the radiation (step S15). Thereafter, the control device 22 transitions to the reading mode, and reads the data (dark image data) of the offset signal value due to the dark charge, from the radiation detecting elements 7 (dark reading) (step S16).

In the process of step S14 to step S16, which is the dark image acquiring process, the dark image data is acquired.

The image data of the radiation image and the dark image data that are acquired by the above process are sent to the console 58, and image processes such as the offset correction of the radiation image using the dark image data are performed.

Figure 12:
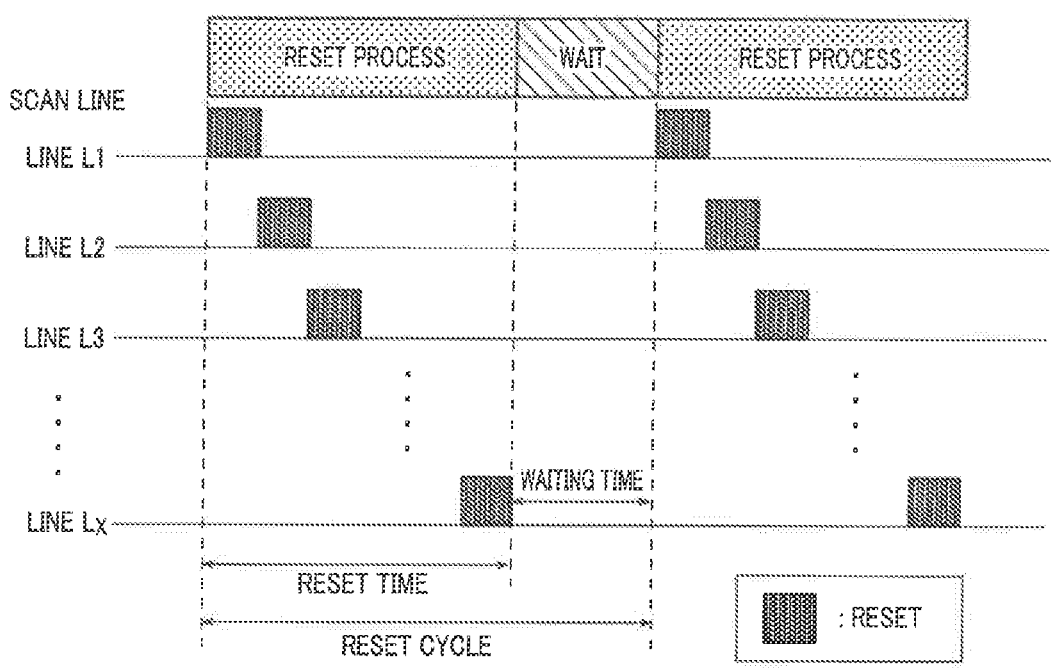
FIG. 12 is a diagram for describing a reset time, a waiting time and a reset cycle in the embodiment.
Figure 13A:
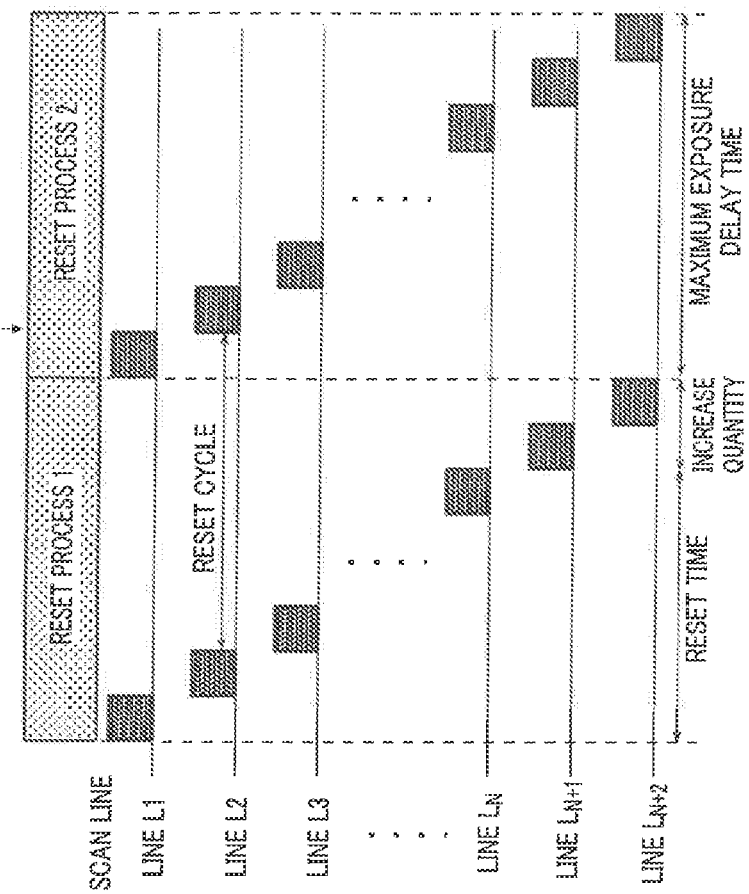
FIG. 13A is a diagram for describing the line number of scan lines and the maximum exposure delay time in conventional apparatuses.
Figure 13B:
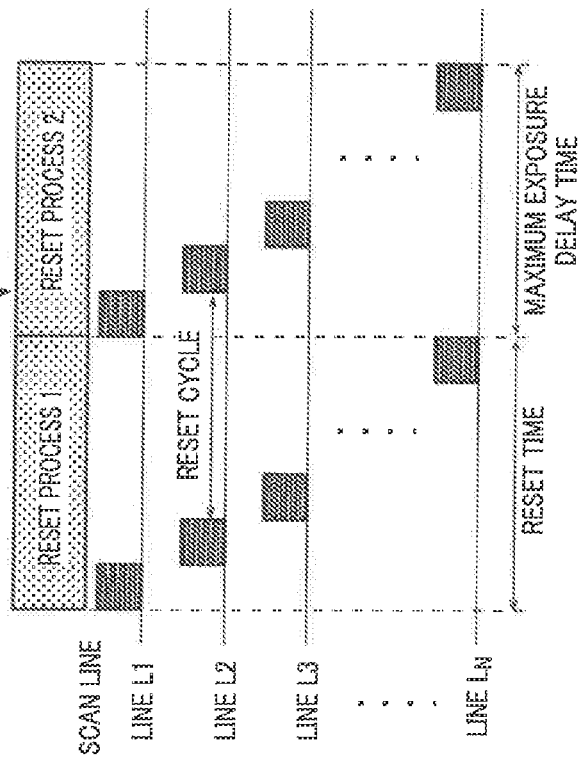
FIG. 13B is a diagram for describing the line number of san lines and the maximum exposure delay time in recent high-definition radiation image photographing apparatuses.

Thus, in the radiation image photographing apparatus 1, as shown in FIG. 12, the waiting time for causing all the TFTs 8 on the lines L1 to Lx to wait in the off-state is provided in the period between the reset processes (before the main photographing) in the radiation image photographing process (in the period after the reset of the last line Lx is completed and before the next reset of the first line L1 is started), so that the reset cycle is prolonged compared to the reset time. Therefore, as shown in the graph of FIG. 9 showing the temporal change in offset signal value associated with the on/off switching of the TFTs 8, it is possible to secure the time until the offset signal value once increased by the turn-on of the TFTs 8 sufficiently decreases, and it is possible to suppress the cumulative increase in offset signal value. As a result, even in the case of a short reset time, it is possible to suppress the gap between the offset signal value included in the image data of the radiation image and the offset signal value of the dark image data, and it is possible to accurately perform the offset correction.

When the second button 56*a*2 is depressed during the waiting time, the waiting mode is forcibly stopped, and after a predetermined number of reset processes, the transition to the charge accumulation mode is performed. Therefore, it is possible to suppress the increase in the maximum exposure delay time due to the waiting time.

When the wait is stopped, the decrease quantity of the offset signal value is smaller than when the wait is performed for the waiting time. However, the offset signal value in each radiation detecting element 7 at the start of the main accumulation is smaller compared to the cumulative increase in offset signal value due to the continuous reset. Further, by experiments, it has been confirmed that the remaining offset signal value due to the stop of the wait has no influence on the diagnosis.

The embodiment of the invention has been described above. The description in the above embodiment is a preferred example of the present invention, and the present invention is not limited to this.

For example, in the above embodiment, the radiation image photographing apparatus that switches from the reset mode to the charge accumulation mode in cooperation with the radiation generating apparatus has been described as an example of the present invention. However, the present invention may be applied to a self-detection type radiation image photographing apparatus that has a function to detect the start of the radiation irradiation. When the start of the radiation irradiation is detected, the self-detection type radiation image photographing apparatus stops the reset process in execution or the wait, and immediately transitions to the charge accumulation mode. When the present invention is applied as described above, it is possible to reduce the offset signal value in each radiation detecting element 7 at the start of the main accumulation, compared to the cumulative increase in offset signal value due to the continuous reset process, and it is possible to suppress the gap between the offset signal value included in the image data of the radiation image and the offset signal value of the dark image data.

In the above embodiment, the radiation image photographing apparatus that performs the dark image acquiring process following the radiation image photographing process has been described as an example. However, the present invention may be applied to a radiation image photographing apparatus (including the self-detection type) that performs the dark image acquiring process before the radiation image photographing process. Also in this case, similarly, it is possible to reduce the offset signal value in each radiation detecting element 7 at the start of the main accumulation, compared to the cumulative increase in offset signal value due to the continuous reset process, and it is possible to suppress the gap between the offset signal value included in the image data acquired by the main photographing and the offset signal value of the dark image data.

The present invention may be applied to a radiation image photographing apparatus that performs a binning process of reading signals of the radiation detecting elements on a plurality of adjacent lines of the scan lines at the same timing and averaging or adding the signals. When the binning process is performed, since the reading is performed collectively for the plurality of lines, the necessary waiting time changes compared to when the reading is performed for each line. Therefore, the increase in binning number increases the gap in offset signal value. By providing a waiting time corresponding to the number of lines for which the reading is collectively performed, it is possible to suppress the gap between the offset signal value included in the image data acquired by the main photographing and the offset signal value of the dark image data.

In addition, the detailed configurations and detailed operations of the apparatuses that constitute the radiation image photographing system can be modified when appropriate, without departing from the spirit of the present invention.

Although embodiments of the present invention have been described and illustrated in detail, the disclosed embodiments are made for purposes of illustration and example only and not limitation. The scope of the present invention should be interpreted by terms of the appended claims.

The description, claims, drawings and abstract of Japanese Patent Application No. 2018-026727 filed to Japan Patent Office on Feb. 19, 2018 are incorporated herein by reference in its entirety.

What is claimed is:

1. A radiation image photographing apparatus comprising:
   a plurality of scan lines;
   a plurality of signal lines that are arranged so as to intersect the plurality of scan lines;
   radiation detecting elements that are two-dimensionally arrayed in regions separated by the plurality of scan lines and the plurality of signal lines;
   switches, each of the switches being disposed for a respective one of the radiation detecting elements;
   a scan driver including a gate driver and a power supply circuit that supplies an on-voltage and an off-voltage to the gate driver;
   wherein the gate driver is configured to switch each of the switches between an off-state and an on-state by switching a voltage to be applied to one of the plurality of scan lines connected with each of the switches between the off-voltage and the on-voltage,
   each of the switches being configured to respectively cause a charge generated in each of the radiation detecting elements to be accumulated in each of the radiation detecting elements in the off-state, and each of the switches being configured to respectively cause the charge to be released from each of the radiation detecting elements to one of the plurality of signal lines connected to each of the radiation detecting elements in the on-state;
   a reading circuit that performs an image data reading process of reading image data from each of the radiation detecting elements by converting the charge released from each of the radiation detecting elements into the image data; and
   a hardware processor that performs a radiation image photographing process and a dark image acquiring process by controlling at least the scan driver and the reading circuit, wherein
   at a time of the radiation image photographing process, the hardware processor repeats a reset process of releasing the charge from each of the radiation detecting elements and resetting each of the radiation detecting elements by sequentially applying the on-voltage from the scan driver to the plurality of scan lines until a radiation irradiation is started, provides a waiting mode in which the switches wait in the off-state after the reset process is ended and before a next reset process is started for a predetermined waiting time, transitions to a charge accumulation mode of accumulating the charge in each of the radiation detecting elements by applying the off-voltage from the scan driver to the plurality of scan lines in response to a start of the radiation irradiation, and transitions to a reading mode of releasing the charge from each of the radiation detecting elements by applying the on-voltage from the scan driver to the plurality of scan lines, and performing the image data reading process by converting the charge released to the reading circuit into the image data when a predetermined accumulation time has elapsed, and
   at a time of the dark image acquiring process, the hardware processor transitions to the charge accumulation mode to wait in a state where the radiation irradiation is not performed, after a reset process is performed, and transitions to the reading mode when a predetermined time has elapsed.

2. The radiation image photographing apparatus according to claim 1, wherein when the radiation irradiation is started during an ongoing reset process, the hardware processor transitions to the charge accumulation mode after a completion of the ongoing reset process, and when the radiation irradiation is started during waiting mode, the hardware processor transitions to the charge accumulation mode after the hardware processor forcibly stops the waiting mode before the waiting mode has elapsed and performs a reset process.

3. The radiation image photographing apparatus according to claim 1, wherein when the hardware processor receives a signal that indicates a depression of a first button of an exposure switch the hardware processor starts a reset process in the radiation image photographing process, and when the hardware processor receives a signal that indicates a depression of a second button of the exposure switch the hardware processor transitions to the charge accumulation mode.

4. The radiation image photographing apparatus according to claim 1, wherein the hardware processor provides the wait mode between each successive pair of reset processes performed before the charge accumulation mode.

5. A radiation image photographing system comprising:
a radiation image photographing apparatus according to claim 1; and
a radiation source to irradiate the radiation image photographing apparatus with a radiation.

6. A radiation image photographing apparatus comprising:
a plurality of scan lines;
a plurality of signal lines that are arranged so as to intersect the plurality of scan lines;
detecting elements that are two-dimensionally arrayed in regions separated by the plurality of scan lines and the plurality of signal lines;
switches, each of the switches being disposed for a respective one of the radiation detecting elements;
a scan driver including a gate driver and a power supply circuit that supplies an on-voltage and an off-voltage to the gate driver;
wherein the gate driver is configured to switch each of the switches between an off-state and an on-state by switching a voltage to be applied to one of the plurality of scan lines connected with each of the switches between the off-voltage and the on-voltage,
each of the switches being configured to respectively cause a charge generated in each of the radiation detecting elements to be accumulated in each of the radiation detecting elements in the off-state, and each of the switches being configured to respectively cause the charge to be released from each of the radiation detecting elements to one of the plurality of signal lines connected to each of the radiation detecting elements in the on-state;
a reading circuit that performs an image data reading process of reading image data from each of the radiation detecting elements by converting the charge released from each of the radiation detecting elements into the image data; and
a hardware processor that performs a radiation image photographing process by controlling at least the scan driver and the reading circuit, wherein
at a time of the radiation image photographing process, the hardware processor repeats a reset process of releasing the charge from each of the radiation detecting elements and resetting each of the radiation detecting elements by sequentially applying the on-voltage from the scan driver to the plurality of scan lines until a radiation irradiation is started, provides a waiting mode in which the switches wait in the off-state after the reset process is ended and before a next reset process is started for a predetermined waiting time, transitions to a charge accumulation mode of accumulating the charge in each of the radiation detecting elements by applying the off-voltage from the scan driver to the plurality of scan lines in response to a start of the radiation irradiation, and transitions to a reading mode of releasing the charge from each of the radiation detecting elements by applying the on-voltage from the scan driver to the plurality of scan lines, and performing the image data reading process by converting the charge released to the reading circuit into the image data when a predetermined accumulation time has elapsed.

* * * * *